United States Patent [19]
Henco et al.

[11] Patent Number: 5,871,908
[45] Date of Patent: *Feb. 16, 1999

[54] PROCESS FOR THE DETERMINATION OF IN VITRO AMPLIFIED NUCLEIC ACIDS

[75] Inventors: Karsten Henco, Erkrath; Manfred Eigen, Gottingen; Detlev Riesner, Dusseldorf, all of Germany

[73] Assignee: Evotec BioSystems GmbH, Hamburg, Germany

[ * ] Notice: The terminal 14 months of this patent has been disclaimed.

[21] Appl. No.: 157,195

[22] PCT Filed: Feb. 4, 1993

[86] PCT No.: PCT/EP93/00254

§ 371 Date: Dec. 8, 1993

§ 102(e) Date: Dec. 8, 1993

[87] PCT Pub. No.: WO93/16194

PCT Pub. Date: Aug. 19, 1993

[30]     Foreign Application Priority Data

Oct. 9, 1992 [DE] Germany .................. 42 34 086.1
Feb. 4, 1993 [DE] Germany .................. 42 03 178.8

[51] Int. Cl.[6] ................ C12Q 1/68; C12P 19/34
[52] U.S. Cl. ......................... 435/6; 435/912
[58] Field of Search ............ 435/6, 91.2; 536/26.6

[56]     References Cited

U.S. PATENT DOCUMENTS 5,184,020  2/1993  Hearst et al. .............. 250/455.11

FOREIGN PATENT DOCUMENTS

| 0381501 | 8/1990 | European Pat. Off. . |
|---|---|---|
| 9201533 | 2/1992 | Japan . |
| 9001563 | 2/1990 | WIPO . |
| 9005023 | 5/1990 | WIPO . |
| 9015881 | 12/1990 | WIPO . |
| 9102815 | 3/1991 | WIPO . |
| 9102817 | 3/1991 | WIPO . |

OTHER PUBLICATIONS

Y. Jinno et al., "Use of psoralen as extinguisher of contaminated DNA in PCT", Nucleic Acids Research, Bd. 18, Nr. 22, p. 6739.

K. Henco et al., "Quantitative PCR: the determination of template copy numbers by temperature gradient gel electrohoresis (TGGE)", Nucleic Acids Research, Bd. 18, Nr. 22, pp. 6733–6734, 1990.

J.E. Hearst, "A photochemical investigation of the dynamics of the oligonucleotide hybridization", Ann. Rev. Phys. Chem., Bd. 39, pp. 291–315, 1988.

Kingsbury et al., "Rapid Detection and Identification of Infection Agents", Academic Press, Inc., pp. 245–256, 1985.

*Primary Examiner*—Kenneth R. Horlick
*Attorney, Agent, or Firm*—Jacobson, Price, Holman & Stern, PLLC

[57]     ABSTRACT

A process for the qualitative and quantitative determination of at least one in vitro amplified nucleic acid in a sealed reaction chamber, wherein during or subsequent to the amplification of the nucleic acid at least one substance (probe) is present which interacts with the nucleic acid to be detected;

wherein spectroscopically measurable parameters of said substance (probe) are subject to variation, creating a measurable signal;

wherein the sample to be measured is exposed to the action of a gradient capable of at least partially denaturing nucleic acids;

with detection of the measurable parameter undergoing variation through the action of the gradient; and the entire amplification reaction, including qualitative and quantitative determination, may be carried out in a sealed reaction chamber (measuring compartment) without intermittent opening, permitting to automatically operate the diagnostic method of DNA and RNA amplification in qualitative and quantitative fashion on large series of samples.

43 Claims, 13 Drawing Sheets

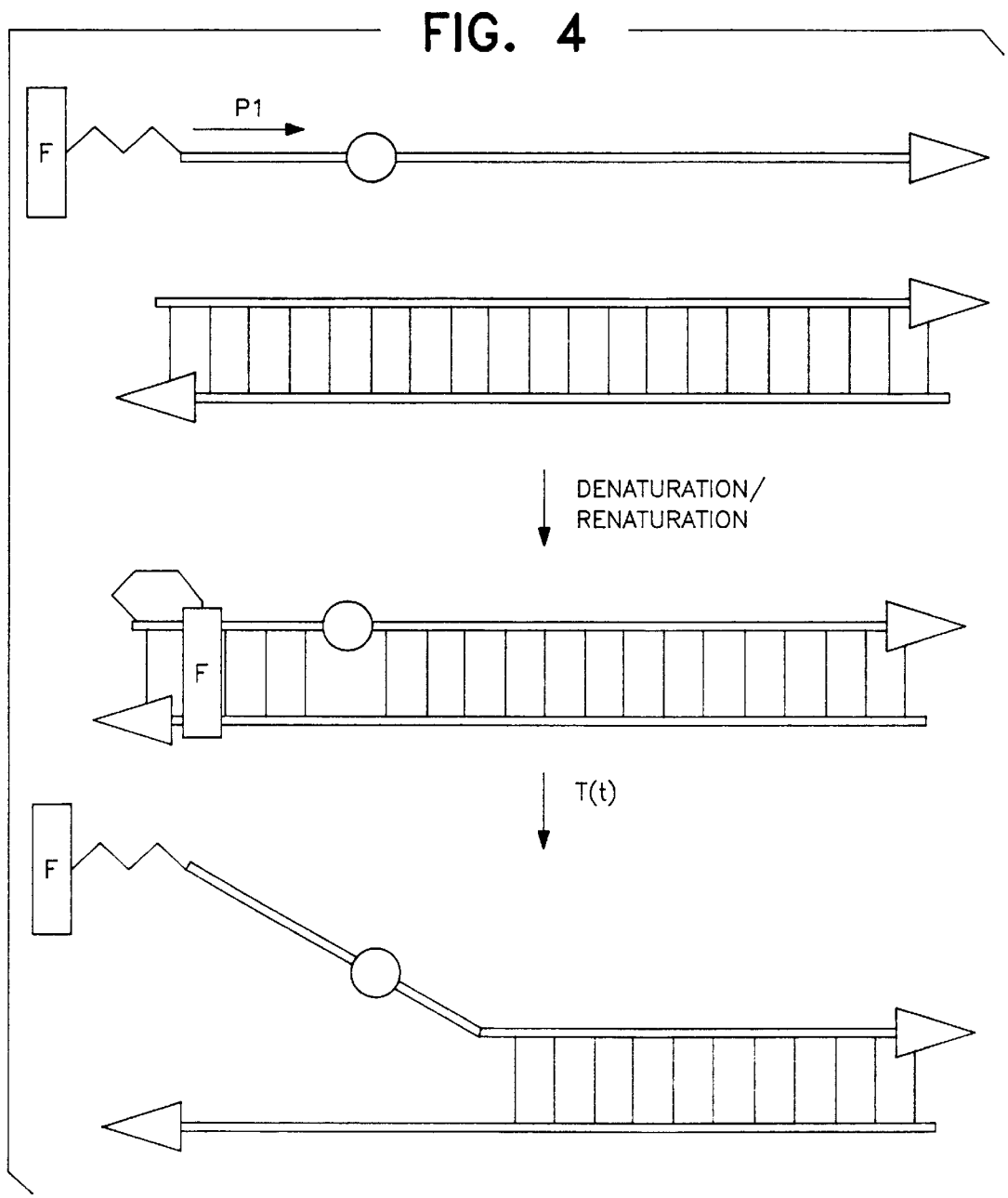

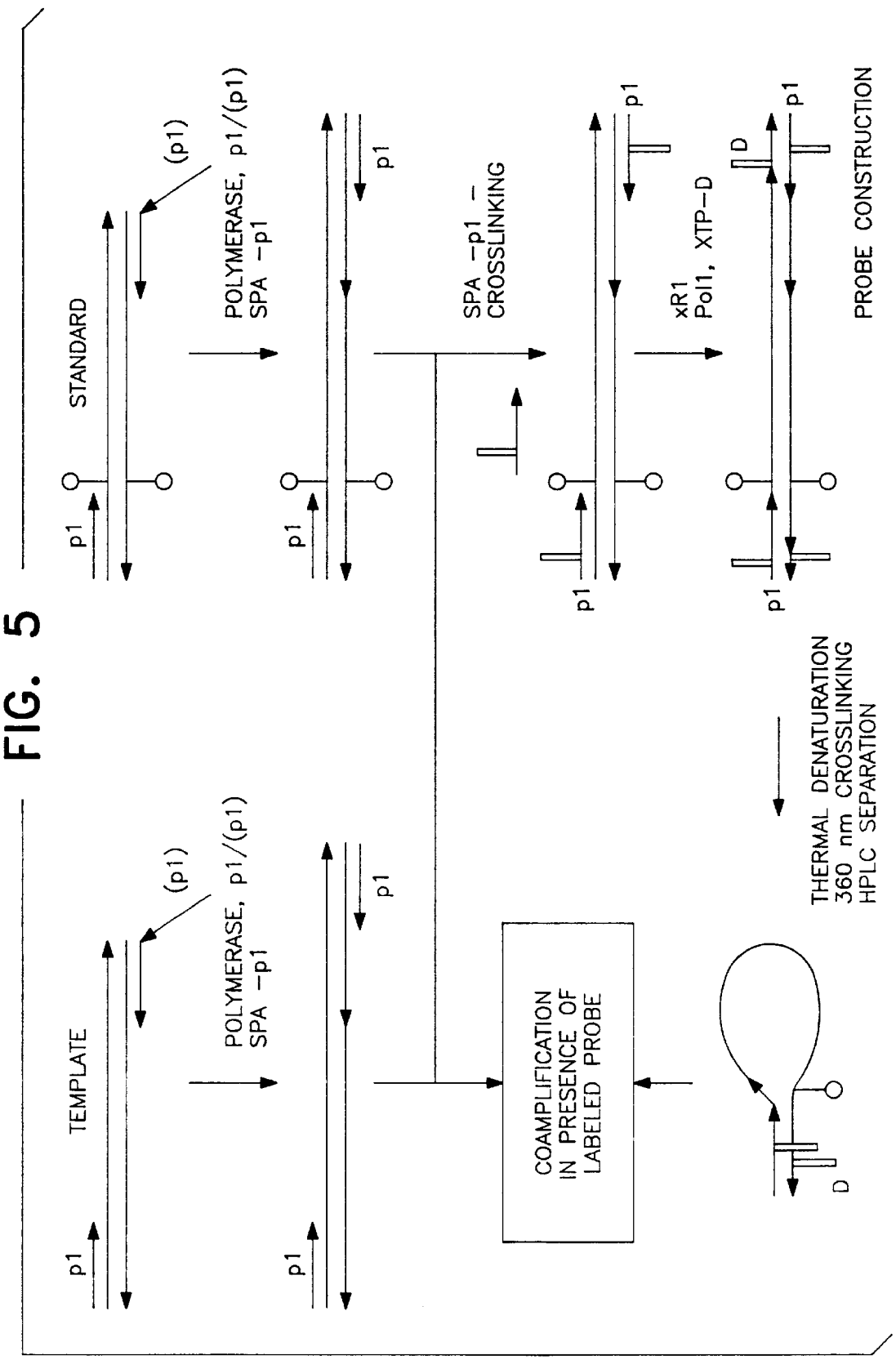

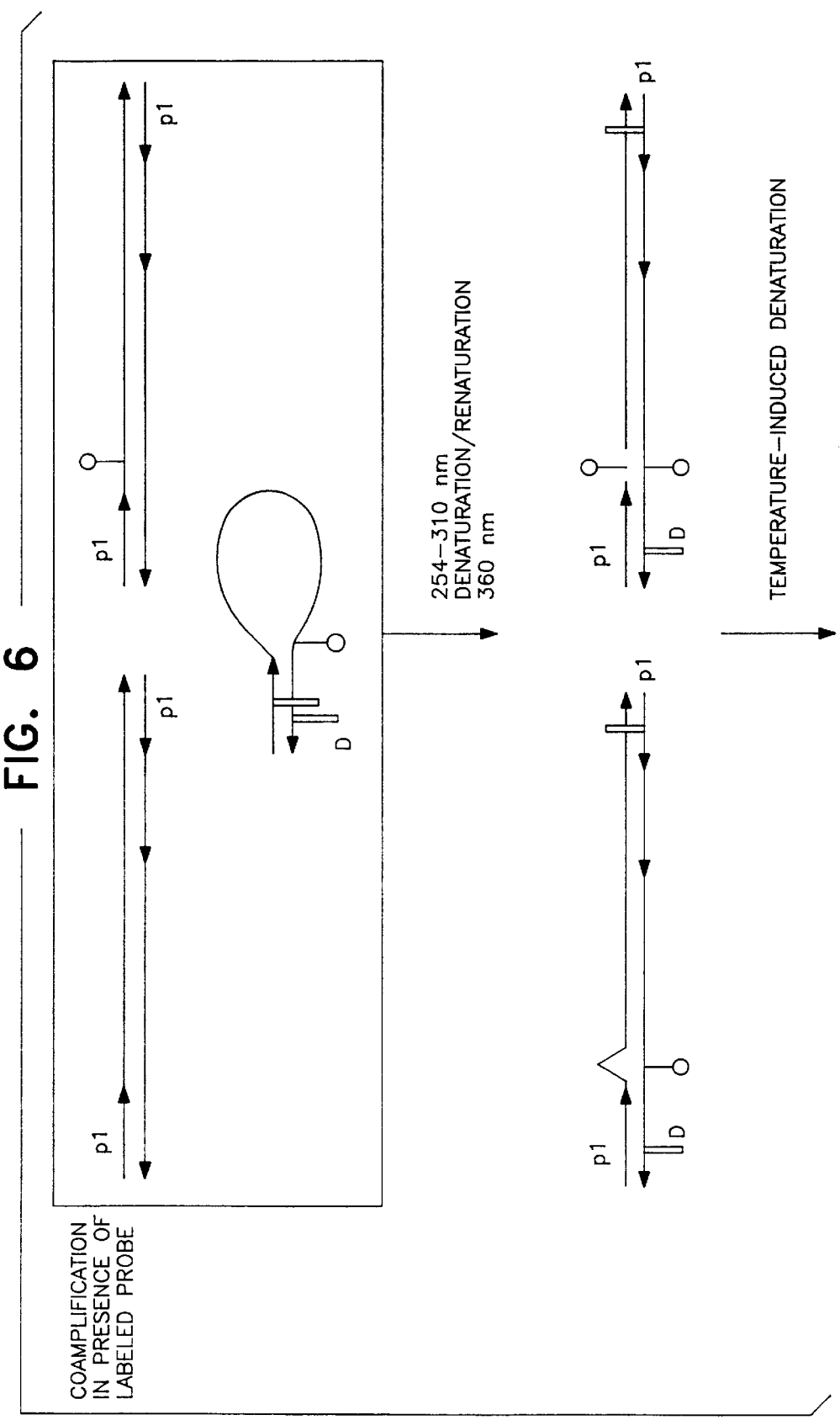

PROBE CONSTRUCTION

CROSSLINKED HETERODUPLEX

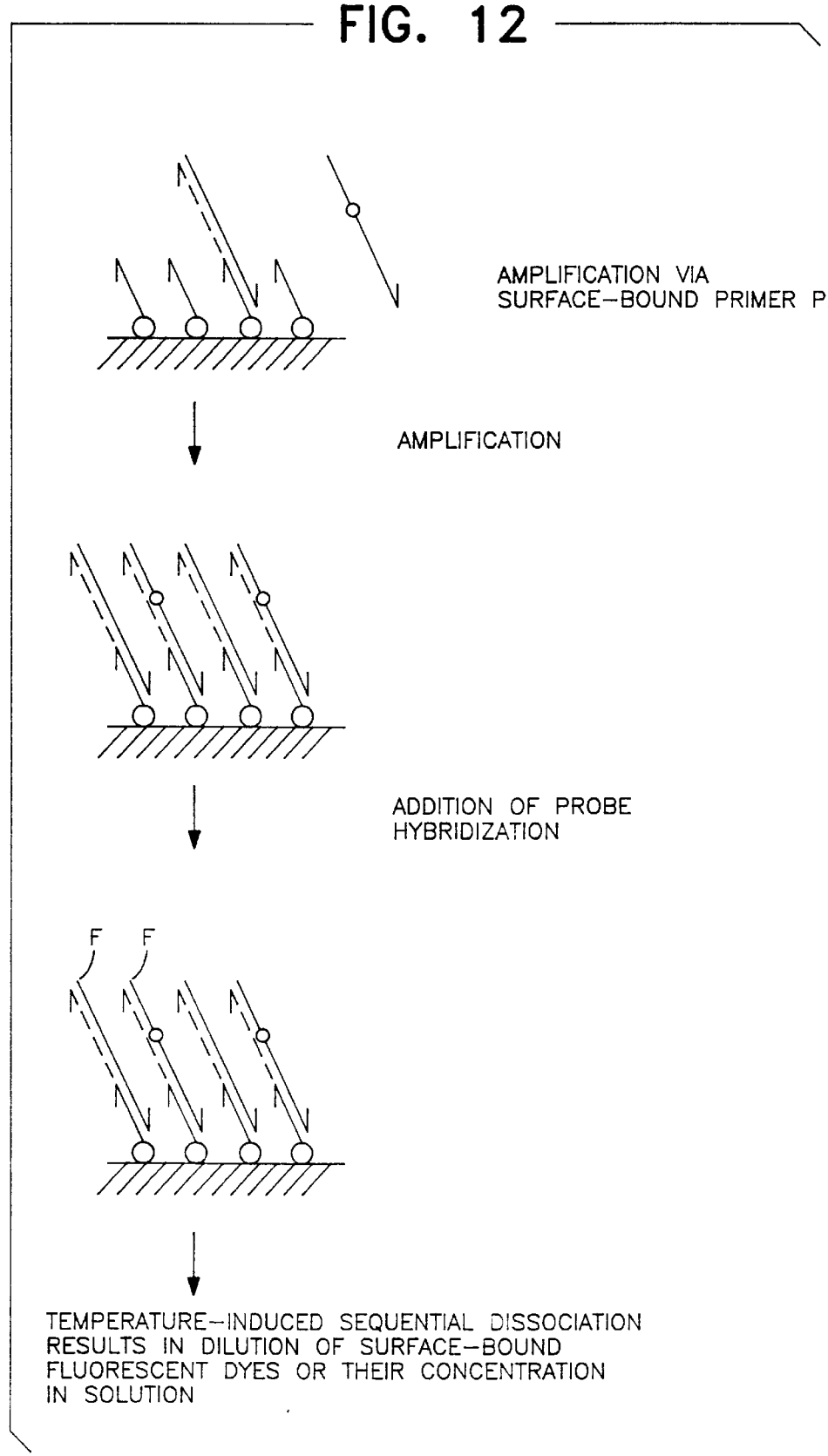

PROCESS FOR THE DETERMINATION OF IN VITRO AMPLIFIED NUCLEIC ACIDS

This invention is directed to a process for determining at least one in vitro amplified nucleic acid in a reaction chamber, a device suitable for operating the process of the invention, and means for operating the process of the invention.

Increasingly, modern analytics returns to basic principles of molecular biology. Very recently, the polymerase chain reaction (PCR) was found to be a very useful tool for analytics utilizing basic principles of molecular biology, and is applicable to all the fields of analytics where nucleic acids play a direct or indirect role.

In principle, PCR analytics [R. K. Saiki et al. Science 239, 487–491 (1988)] and other enzymatic amplification techniques [J. C. Guatelli et al., Proc. Natl. Acad. Sci. 87, 1874–1878 (1990)] are able to detect low titers of DNA or RNA copies in aqueous solution. Ultimately, a single copy is sufficient for enzymatic amplification. However, a number of problems have shown in routine qualitative application as well as in the efforts to combine PCR with a quantitative copy number determination. The difficulties of amplification analytics are associated with:

- undesirable amplification by mispriming;
- non-uniform primer consumption;
- heteroduplex formation;
- varying cycle efficiencies;
- various amplification artifacts;
- problems in quantification;
- risk of contamination;
- "erroneously positive" results;
- "erroneously negative" results;
- cost of testing;
- readiness for application in series;
- expenses in handling as compared to the immunological ELISA process for protein analytics.

WO 91/02815 describes the reliable qualitative and quantitative detection of specific DNA and RNA from biological sample material using a DNA/RNA amplification method in combination with, e.g., temperature gradient gel electrophoresis [cf., K. Henco & M. Heibey Nucleic Acids Res. 19, 6733–6734 (1990); J. Kang et al. Biotech. Forum Europe 8, 590–593, (1991); G. Gilliland et al. Proc. Natl. Acad. Sci. 87, 2725–2729 (1990)].

By way of the amplification strategy described in WO 91/02815 it has been accomplished to combine the sensitivity of the amplification techniques with reliable and extremely precise quantification (variation ±15%). The method allows for controlling or overcoming the above-mentioned problems as are occurring with amplification processes. Using a nearly ideal internal standard of a defined number of copies, which standard differs from the template to be determined in only one single base position, amplification may be carried out with the initial ratio of template and standard being maintained [K. Henco and M. Heibey, Nucleic Acids Res. 19, 6733–6734 (1990)]. Template and standard are made subsequently in a temperature gradient process using a time- or space/temperature gradient in the gel electrophoresis system. The ratio of template and standard may be determined in a simple fashion by hybridizing the reaction mixture with a radioactive-labeled or fluorescent-labeled standard. Heteroduplex formation, in other cases occurring interferingly, cannot distort the results in such system. Rather, heteroduplex formation is utilized for the actual measurement.

Usual problems caused by non-uniform consumption of primers, mispriming reactions, saturation effects, and variations in amplification efficiency do not have any negative influence on the results of quantification.

This technology has been applied to major analytical issues in medicine. Thus, for example, it has become possible to quantifyingly detect cytomegalic infections or viremia in transplanted patients or newborn children. Here, the process has proven particularly worthwhile since, in view of infection rates in the European countries of more than 90% here and there, the sole detection of cytomegalic viruses is of minor importance if not a titer determination is carried out simultaneously indicating the acute condition of viremia. With viral diseases, the quantifying aspect is gaining significance, particularly in context with the increasingly applied models of antiviral therapy. Frequently, antiviral therapies, as for instance in the case of HIV using AZT, are systemically extremely straining for the patient and, as an antiviral therapeutic agent, can only be employed for a limited period of time. In future, therefore, it will be very important to have an economic and simple technique allowing for both titer determination or determination of virus gene activity and indicating therapy-induced drift to resistant virus strains.

Having from small to low sample numbers (10–20), hitherto applied gel electrophoretic methods for separating the marked homoduplexes and heteroduplexes have proven extraordinarily efficient and correct with respect to the results supplied. However, a severe drawback is the relatively time- and personnel-intensive analytical technique making it difficult to employ this very profound analytical technique as a general diagnostic method for DNA and RNA analytics. Using the temperature gel electrophoretic technique, it is hardly possible to perform sample numbers>50 per operating person and day. Likewise, automatization is but difficult to achieve.

Thus, it is an object of the invention to provide a process which avoids the above-mentioned disadvantages of prior art processes and, more specifically, to design a detection process for nucleic acids in such fashion that gel electrophoretic separation is not required, in order to ensure a more simple and automatable procedure. At the same time it is intended to create a device allowing for reliable and simple observation of the detected amplified nucleic acids using the process of the invention, where the device is to allow automatable evaluation to the largest extent.

According to the invention, this problem is solved by a process for the qualitative and quantitative determination of at least one in vitro amplified nucleic acid in a sealed reaction chamber, wherein during or subsequent to the amplification of the nucleic acid at least one substance (probe) is present which interacts with the nucleic acid to be detected;

wherein spectroscopically measurable parameters of said substance (probe) are subject to variation, creating a measurable signal;

wherein the sample to be measured is exposed to the action of a gradient capable of at least partially denaturing nucleic acids;

with detection of the measurable parameter under-going variation through the action of the gradient; and the entire amplification reaction, including qualitative and quantitative determination, may be carried out in a sealed reaction chamber (measuring compartment) without intermittent opening.

The substance (probe), the parameter of which is to be detectable spectroscopically, preferably contains at least one fluorescent residue, preferably having intercalating properties, and a nucleic acid proportion. The interaction with the in vitro amplified nucleic acid as a function of the denaturation condition is accompanied by a change in the spectroscopically measured signal. This, for example, may take place by intercalation of the dye into the nucleic acid double helix or by dilution or concentration effects within the measuring compartment.

In another preferred embodiment of the process according to the invention, the nucleic acid denaturation process initiated by the gradient is detected using wave length variation and/or shift in fluorescent intensity and/or variation in excited state lifetime, or using the principle of the so-called energy transfer (Förster Transfer), or via concentration effects, or using various, preferably hydrophobic interactive properties of the labeled probe.

Likewise, the process of the invention permits simultaneous or sequential detection of multiple different amplified nucleic acids. This is effected by using a multiplicity of dyes which may be distinguished from each other spectroscopically, which permit to analyze the various amplified nucleic acids and/or through which at least one independent calibrating substance is introduced. This, in particular, is possible where the various nucleic acids to be analyzed interact with differently labeled participants in hybridization.

Registration of the measuring signal is conducted, for instance, by measuring the fluorescence generated by the dyes which, in particular, may be excited continuously or in pulses by a laser.

A further preferred embodiment of the process according to the invention is based on that the amplified nucleic acids contain at least one co-amplified nucleic acid standard, the sequence of which is homologous to a sequence to be determined and preferably identical, however, with the exception of at least one point mutation which, in particular, lies in a sequence region of lowest stability. However, care must be taken that the point mutation lies outside the primer binding sites if enzymatic amplifications are performed. The nucleic acid standard may also be a natural component of the nucleic acid to be analyzed.

According to the invention, it is also possible to observe successful amplification of a specific nucleic acid without adding a labeled standard fragment to the reaction batch after amplification has taken place. In this preferred procedure of the invention, specifically those primers required for amplification are employed (EP-A-0,469,755) which then hybridize at the corresponding sites in the sequence of the nucleic acids in question. However, the corresponding sequences between the primer sites may be so different that when passing the temperature gradient, both sequences—the amplified test and standard sequence—denature separately, and preferably, denature in co-operative fashion.

This allows use of sequences having a sequence deviation to such extent that heteroduplex formation is no longer possible. Thus, it is no longer necessary to add a labeled standard fragment after amplification has taken place. Different melting temperatures of both sequences may be influenced, for example, by greatly varying the length of the sequence or by selecting a poly-A/T-sequence. The question whether an amplification reaction has taken place may then be decided by employing the process of the invention, for example, in a temperature gradient with simultaneous presence of ethidium bromide, where quantitative detection is likewise possible.

The process according to the invention permits to perform the amplification in homogenous phase or on a solid phase, preferably using a primer attached to a solid phase, to the extended sequence of which the labeled probe can hybridize. Thus, the concentration of the probe can be determined either specifically at the solid phase support or within the free solution. Preferably, at least one molecule of fluorescent dye is linked to a nucleic acid molecule, the sequence of which is identical or homologous to the nucleic acid to be detected or to the co-amplified nucleic acid standard.

Once the nucleic acid molecule with the fluorescent dye linked thereto has been added to the reaction mixture after amplification has taken place, hybridization with the amplified nucleic acids is effected, preferably by a thermal denaturation step with a subsequent renaturation step. According to the invention, however, it is also possible to add the nucleic acid molecule having the linked fluorescent dye to the reaction mixture before amplification has taken place. Here, the probe is to be added as a non-amplifiable double-stranded RNA or as a non-amplifiable chemically modified nucleic acid.

For nucleic acid amplification, a possible embodiment uses a primer of the primer pair employed for amplification, which primer contains a G:C-rich region at the 5' terminus, for example from 15 to 20 G:C residues.

The standardization and quantification of the process according to the invention by the above preferred embodiments of the, for instance, fluorescent probes as described so far, involves a tolerable limitation. Thus, the probes used for standardization may be added only subsequent to effected amplification. This means that initially, during the amplification reaction they must be stored spatially separated from the amplification process. Likewise, it may be advantageous for various applications to provide probes used as standard nucleic acids and differing in more than one position from the nucleic acid to be determined. In order to improve the signal/noise ratio in the following determination using the employed probe, it is desirable not to be forced to add deficient probe to the mixture to be amplified.

Thus, in a particularly preferred embodiment of the process according to the invention, as the probe there is used an oligo- or polynucleotide as a single-stranded nucleic acid which, however, cannot participate in the amplification reaction because of chemical modification. Only by suitable manipulation following the amplification reaction, the single-stranded probe is exposed and may then hybridize with the corresponding nucleic acids to be determined. Thus, for example, the probe, if present in the form of a single-stranded nucleic acid, may be inactivated in the form of a "hairpin structure" and may thus be prevented from participating in the amplification reaction.

The oligo- or polynucleotides to be used as probes in a particularly preferred fashion have one or more structural elements with at least two chemical substituents, each being capable of interacting with electromagnetic waves, with cleavage or linkage of stable bonds, or by absorption or emission of radiation. As the substituent particularly suitable for interacting with electromagnetic radiation, with cleavage and linkage of stable bonds, specifically covalent bonds, psoralene or its derivatives have proven successful. As the structural elements serving as the actual markers of the probe, particularly luminescent dyes such as fluorescent dyes having high quantum yield such as dyes from the thiazole orange class have proven beneficial. Preferable are dyes having large Stokes shift which, dependent on hybridization condition, alter the luminescent properties.

It may be advantageous that the spectra of the structural elements at the respective sensitive sites which, on the one hand, are to be excited for cleavage and linkage of, for instance, covalent bonds or, on the other hand, are to be regarded as absorption or emission maxima, are apart so far that each excitation will not interfere with the function of the other structural element.

Likewise, it is possible to combine both chemical structures in a single chemical structure if linkage and cleavage of bonds each occur at different wave lengths such as possible maximum fluorescence of this structure. Thus, the respective functions, probe fixation within a non-amplified structure on the one hand, and spectroscopic identification of said structure on the other hand, cannot interfere with each other.

Where two separated structural elements have said separated functions it was found beneficial that they should not fall below a distance of at least 10 nucleotides on the oligo- or polynucleotide strand.

The preferred embodiment of the process according to the invention using the oligo- or polynucleotides of the invention preferably functions in such fashion that the probes are added to the above-described mixture of substances, the amplification reaction is carried out as described, and subsequently, induced by radiation for example, the masked probe is released to hybridize with the amplification product to be determined and, as described, to be detected by a time/temperature gradient in homogenous solution, by temperature gel electrophoresis, or by a chromatographic process, for example.

Using this variant of the process according to the invention, it is possible to perform the analysis in such way that the hybridization labeled probe no longer has to be located separately within the compartment of the reaction chamber in order to add it to the reaction mixture immediately prior to the actual analysis. Thus, it is possible to provide the labeled probe with the other reagents in a form in which it cannot participate in the subsequent amplification process. Thereby, it is no longer necessary to separate amplification mixture and probe within the measuring chamber.

In order to operate the process, sheet-like systems having hollows or recesses serving as reaction chambers (compartments) are preferably used. Preferably, the sheet systems are thermally weldable and suited to accommodate ready-for-use reagent mixtures in freeze-dried or matrix-bound form. Furthermore, direct optical measurement of the reaction chamber contents is possible. Hence, the sheet material is transmittant or transparent at least for specific wave length regions of electromagnetic radiation. Preferably, the reagents needed to perform the process according to the invention are stored in spatially separated matrices, and subsequent to sealing the reaction chamber, are introduced into the reaction process. Preferably, the reaction chambers are separated from each other at a distance of the holes in a commercially available microtitration plate. This has the advantage that equipment suitable for processing microtitration plates may be used in the technology described according to the invention.

In order to analyze a mixture of amplified nucleic acids, preferably a time-controlled temperature gradient is applied after addition of substances needed in the reaction, and the denaturation behavior of the nucleic acids is measured. This is done through the variation of spectroscopic parameters of the substance interacting with the nucleic acid. Variation of the spectroscopic parameter is monitored over time or in equivalent fashion as a function of temperature change.

Evaluation of the function of variation in spectroscopic behavior of the substance interacting with the nucleic acid permits to conclude the presence or number or homology of an examined nucleic acid with the corresponding standard. Preferably, evaluation of these data is done on-line using a data processing system.

In addition to eliminating the above-mentioned drawbacks in prior art, the process according to the invention is advantageous in that amplification of nucleic acids and subsequent analytics may be carried out in a single hermetically sealable reaction compartment. Thereby, disposal of these biological materials without opening the compartments is possible, and a potential source of contamination is eliminated. Furthermore, such procedure also permits storage of test sheets of the above-mentioned type in sealed condition over prolonged periods of time so that archiving of the often valuable substances is made possible. However, storage preferably is done in frozen condition. Likewise, the process according to the invention advantageously permits the experiments to be repeatable, optionally at a later time even after prolonged interim storage, or the amplified mixture to be preparatively processable and analyzable.

The device for performing the process of the invention has a means for time-dependent thermostatting of the reaction chambers to be used in the process. Preferably, the thermostatting is controlled by a programmable unit. The read-out unit of the device according to the invention preferably consists of an optical unit capable of registering photons. Particularly preferred are such units which are suitable for registering emitted fluorescent light. Likewise contemplated are equipments capable of detecting other spectroscopic properties such as nuclear spin or electron spin etc. which can be correlated to conformational changes of the nucleic acid double-helix or other structural variables, or the use of chromatographic procedures. Using the method of hydrophobic interaction chromatography, molecules having hydrophobic ligands, as represented by partially denaturing structures of the substances to be analyzed, may be separated from the duplexes.

The device for operating the process of the invention is capable of accommodating a means for operating the process which is assembled of a system of reaction compartments, preferably a sheet system with ready-to-use reagents in freeze-dried form. Preferably, the reaction compartments are arranged in microtitration form. Preferably, the reagents of the means for operating the process are fixated and/or stored in at least one water-soluble matrix. Preferably, the matrix contains stabilizers such as sugars, particularly trehalose or saccharose. Preferably, the means for operating the process of the invention comprises reaction compartments and/or other reagent reservoirs, amplification primers, buffer components, and at least one polymerase and usual co-factors for performing the amplification reaction. In another preferred embodiment of the means for operating the process of the invention, the reaction chamber or reaction compartment is provided with an additional separate reagent reservoir in a matrix located within the sheet sealing the compartment. Here, preferably, the labeled probe with the buffer substances required for hybridization are stored.

Preferably, the means for operating the process of the invention is arranged in kit systems comprising reaction vessels such as sheet systems with storable and directly usable reagent mixtures, where is merely necessary to charge the reaction vessels with the sample to be analyzed which then in hermetically sealed condition is subjected to an amplification procedure and subsequent analysis.

The process according to the invention is particularly suitable for analyzing mixtures of substances, preferably nucleic acids where at least one component in the temperature region of the time/temperature gradient is subject to thermal conversion. By adding and co-amplifying a standard having precisely known number of copies the process of the invention can be standardized and permits quantitative statements about the amplified nucleic acids of the sample to be examined. Using the process of the invention it is possible, for example, to detect mutations, point mutations, deletions, insertions, and rearrangements within the DNA/RNA nucleic acid. Using the quantitative analysis it is also possible to determine the concentrations of such changes in the nucleic acid. The samples may be derived from most various materials such as live, dead, fossil tissue as well as tissue no longer active in metabolism in vivo, or from body fluids, from in vitro cell cultures, or from environmental samples. The process according to the invention allows for qualitative and quantitative detection of cellular genes and genes of infectious pathogens directly or via their RNA gene products as a wild type sequence or as variants.

Moreover, the process of the invention may also be employed for the examination and determination of potentially toxic substances or potential pharmaceutical agents or chemical or biological pesticides by examining their effect on nucleic acids or their amplifications in cellular or non-cellular systems.

BRIEF DESCRIPTION OF THE DRAWINGS

FIG. 1 is a schematic description of a preferred procedure of the process according to the invention. In a receiver of reaction compartments in the form of a plate for microtitration, the reagents required for specific amplification of a nucleic acid are located, for example, in lyophilized form, including the probe. Merely the sample to be analyzed, for example, in the form of an aqueous solution, is added prior to the amplification reaction. A homogenous solution is prepared.

Subsequently, the reaction compartments are sealed with a second sheet, with the second sheet containing at least one further matrix with reagents not participating in the actual amplification reaction. The sheet is positioned in a thermostatting block in order to carry out the enzymatic amplification reaction. Here, amplifications may be performed both at homogenous temperature and in periodically varying temperature cycles (PCR). Subsequent to amplification, the reaction mixture is contacted with the second reagent reservoir, and a homogenous solution is prepared. Following performance of a denaturation/renaturation process, an optical detection system records the laser-induced luminescence (fluorescence, phosphorescence) as a function of a linear temperature gradient which is time-controlled via the thermoblock. The initial temperature may be, e.g., 5° C. minimum, the final temperature 100° C. maximum.

FIG. 2

The illustration schematically shows the course of the process according to the invention using the example of intercalating dyes on a molecular level, which are not fixated to a nucleic acid probe (e.g., ethidium bromide or thiazole orange dyes). These dyes intercalate under native conditions between adjacent base pairs in double-stranded DNA or RNA. In intercalated condition, the fluorescence yield increases up to 20 fold and the lifetime of the excited state about 10 fold. If such system is subjected to a thermal gradient, the thermodynamically most unstable regions of the nucleic acid helix begin to denature initially. Mispairing as generated in heteroduplex formation destabilizes the corresponding sequence region and results in premature opening of the latter. Dye molecules initially bound in this region will be released, resulting in a decrease of the overall fluorescence signal. Here, the dye concentration is to be selected such that free dye and bound dye are in thermodynamic equilibrium and free dye is present in significant excess. Only at higher temperatures the corresponding sequence region of the homoduplex will open, giving rise to further stepwise decrease of the fluorescence signal. From the intensity ratio of both steps, the relative ratio of amounts of homoduplex and heteroduplex can be determined.

Figure 3A:
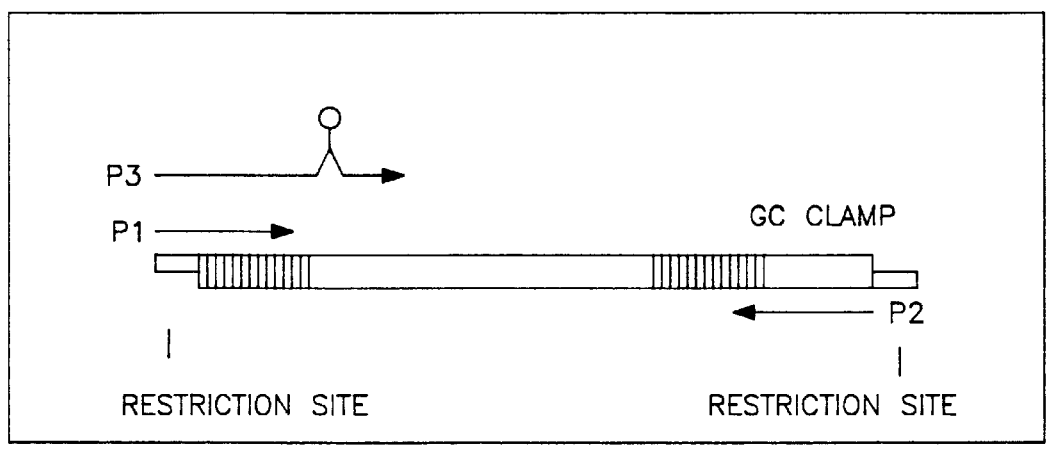
Figure 3B:
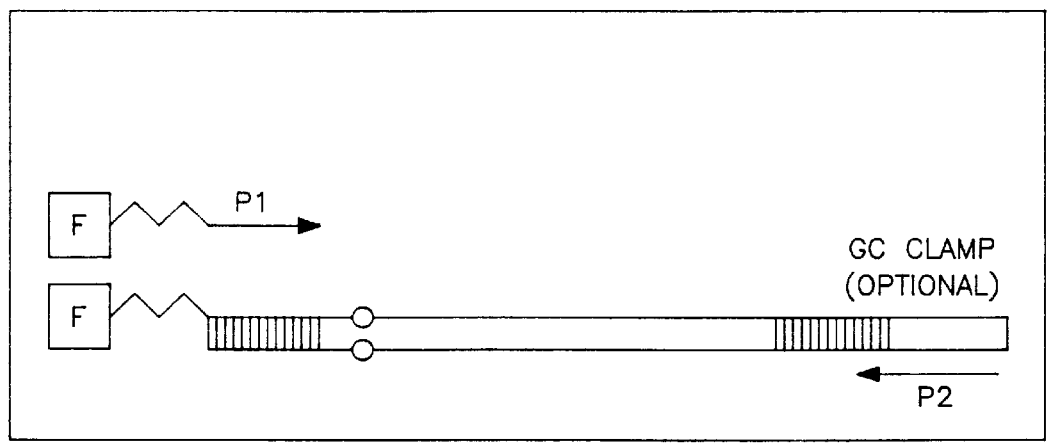

FIGS. 3a and 3b

FIG. 3a illustrates the design of a standard and a fluorescent-labeled probe, respectively, in a preferred embodiment. The standard should differ in at least one base position from the nucleic acid to be detected. Preferably, this mutation is located in the sequence region of lowest thermodynamic stability and may readily be introduced using primer P3. However, the mutation is to be located outside the primer binding sites of P1 and P2. A primer (P2) may contain a GC-rich region at the 5' terminus, while the other primer (P1) preferably is chemically linked through a spacer to a fluorescent dye which may intercalate in the region of the double helix. The application principle of the fluorescent-labeled probe is illustrated schematically in FIG. 3b.

FIG. 4

In a preferred embodiment of the process according to the invention, primers are used as described in Thuong, N. T. & Chassignol, M. Tetrahedron Letters 28, 4157–4160 (1987); Thuong, N. T. et al., Proc. Natl. Acad. Sci. U.S.A. 84, 5129–5133 (1987); Helene, C., in DNA-Ligand Interactions, Plenum Publishing Corporation, 127–140 (1987); W. Gushelbauer & W. Saenger, Ed. Some of them are already commercially available (Appligene, Straβbourg, France). They contain a spacer-linked fluorescent dye capable of intercalating if the primer is located in a double-helical region. Upon thermal denaturation of the double-helix the fluorescent properties of the dye are modified.

FIG. 5

This figure schematically shows a preferred preparation of the probes used in the process of the invention, which are modified and do not participate in the amplification reaction.

The European patent applications EP 0,469,755 and EP 0,379,369 describe the generation of nucleic acid structures. Therein, a structure is generated in representative fashion, the ends of which are complementary to each other. For this purpose, primers p1 and (p1) are employed initially. To prepare the probes, an amplified product is prepared from the corresponding amplified product of the standard using a primer p1 containing the structural element capable of forming stable bonds ("chemical clamp").

Preferably, p1 is selected such that a restriction site having a 5' overhanging end is produced at the 3' side. Thus, following restriction a structure is formed which may be filled up with nucleotides which in turn bear, for instance, a chromophor which is the actual marker of the probe. According to this preparation process, since both strands contain the dye marker and the "chemical clamp", separation of strands and recovery are necessary. However, this does not cause any problems and can be accomplished, for example, by using preparative high pressure liquid chromatography.

Chemical linkage of the complementarily hybridizing ends of the single-stranded hairpin structure is then induced photochemically or chemically, thus preventing template activity of this probe during the phase of enzymatic amplification likewise illustrated in FIG. 5. The probe present in the form of a hairpin loop cannot be involved in the amplification due to its masked structure. Following amplification, for example, when using psoralene derivatives as the "chemical clamp", clamping may be re-opened in the short-wave UV region. Thus, the probe single-strand is released in the denaturation/renaturation process and may be re-linked by repeated irradiation at 360 nm if psoralene derivatives are used. This situation is illustrated schematically in FIG. 6.

If it is possible to induce chemical linkage to the complementary strand by radiation again, this chemical linkage attains a further advantageous function. It can assume the function of the previously used G/C clamp and thus ensure that the hybridized strands during analysis are no longer able to separate from each other, thus enabling irreversible denaturation. As mentioned before, compounds having the psoralene basic structure are preferably used as the "chemical clamp", which possess the property of reacting covalently with pyrimidine bases on activation with light having a wave length of 360 nm. However, there is the proviso that the pyrimidine bases be positioned on the opposite strand, shifted by one base position [J. E. Hearst, Ann. Rev. Phys. Chem., 39, 291–315 (1988)].

Figure 7:
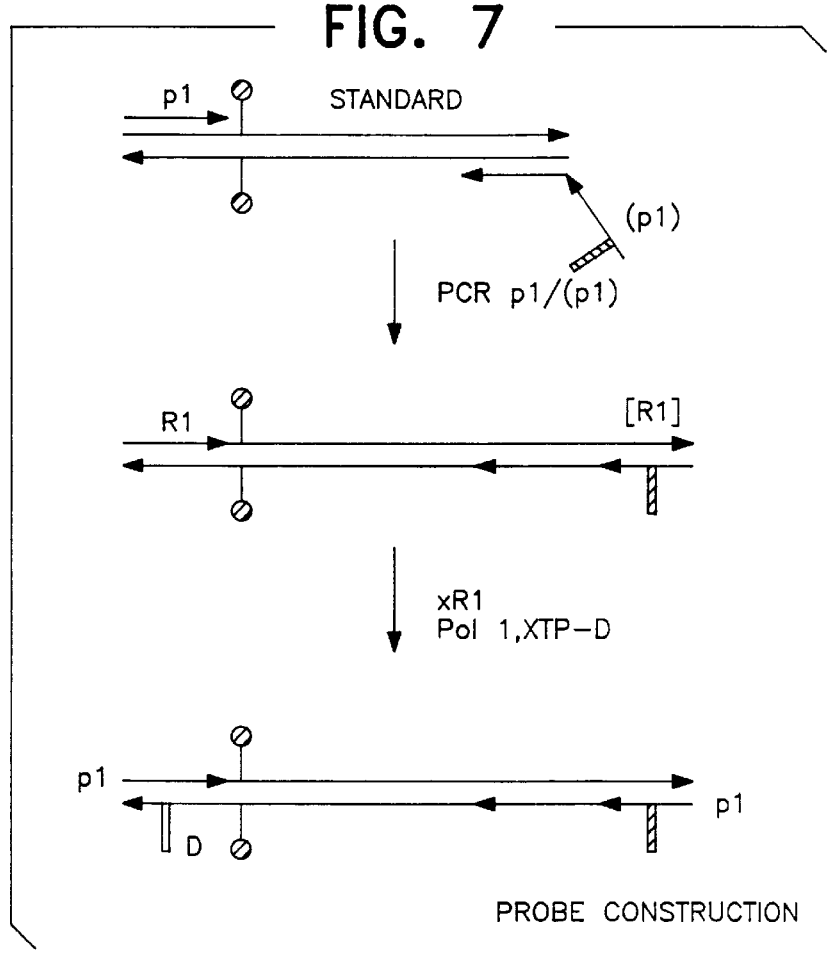

Another alternative in the synthesis of the probe preferred according to the invention is shown in FIG. 7. Here, the "chemical clamp" is introduced via primer (p1). Thus, only the desired strand will later bear the chemical crosslinker. The crosslinker which, in particular, can be activated photochemically, advantageously acts to inactivate the adjacent restriction site of the restriction enzyme R1. In this fashion, it is ensured that subsequently, the dye providing the actual labeling of the probe will be incorporated on the desired strand only. Compared to the above-described probe construction, the somewhat longer primer (p1) with modification is unfavorable.

Figure 8:
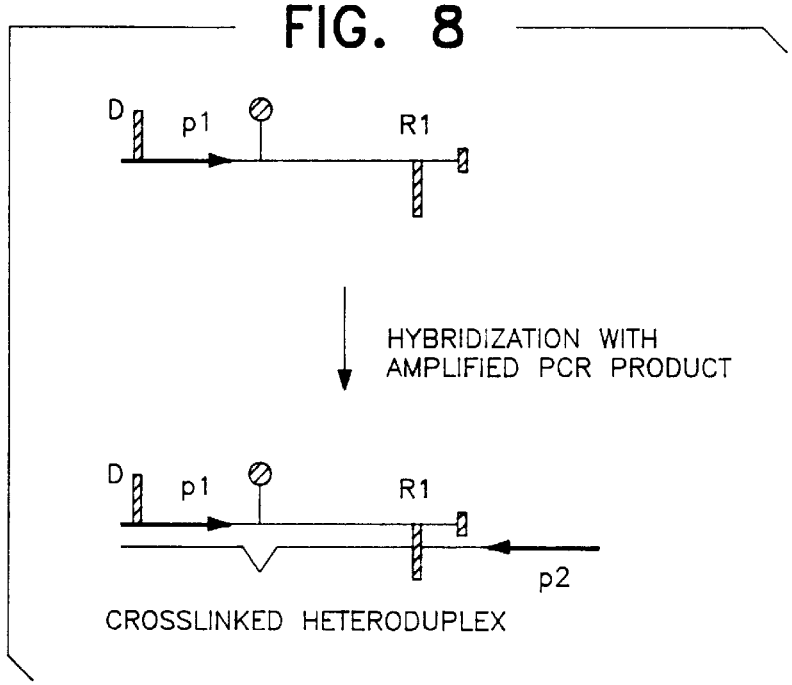

A third possible preferred embodiment of the nucleic acid probe according to the invention is obtained by using a single-stranded probe likewise having a crosslinked ligand, the position of which, however, being located at the 3' end, while the labeling dye molecule is incorporated at the 5' end. This situation is illustrated in FIG. 8. In this case, the probe is constructed such that the primer binding site is missing at the 3' end, the 5' end is identical with the p1 primer sequence, and the 3' end cannot be extended enzymatically, for example, by incorporating a dideoxy-nucleotide at the terminus. The crosslinking agent spatially separates the homologous double-strand region having the marker structural element from the hybrid single-strand region not bearing same. If the single-strand region is not uniformly synthesized as a consequence of an inaccurate amplification process, this will not adversely affect the result of probe construction.

Following this approach of probe construction, the probe will not participate in the amplification process because it is not extendable at the 3' end and thus, even in case of intermediate hybridization with amplified counter-strand, no elongated primer binding site will be synthesized enzymatically.

Thus, following amplification the crosslinking ligand does not have to be liberated initially from a crosslinking structure by irradiating to be subsequently re-crosslinked with amplified product in the re-hybridized structure; a single irradiation procedure is sufficient to cause crosslinking with the amplified product.

FIGS. 9a–e

Figure 9A:
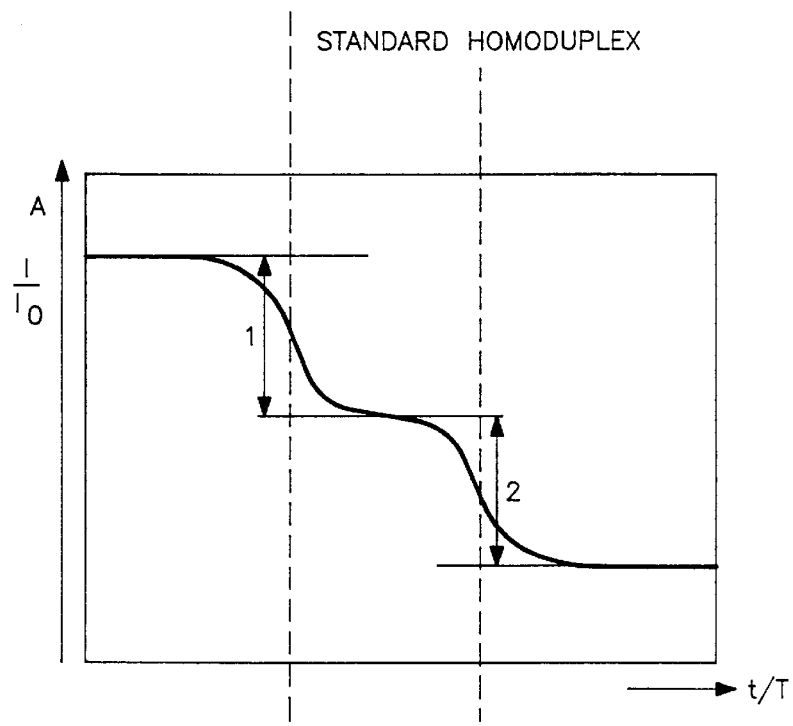
Figure 9B:
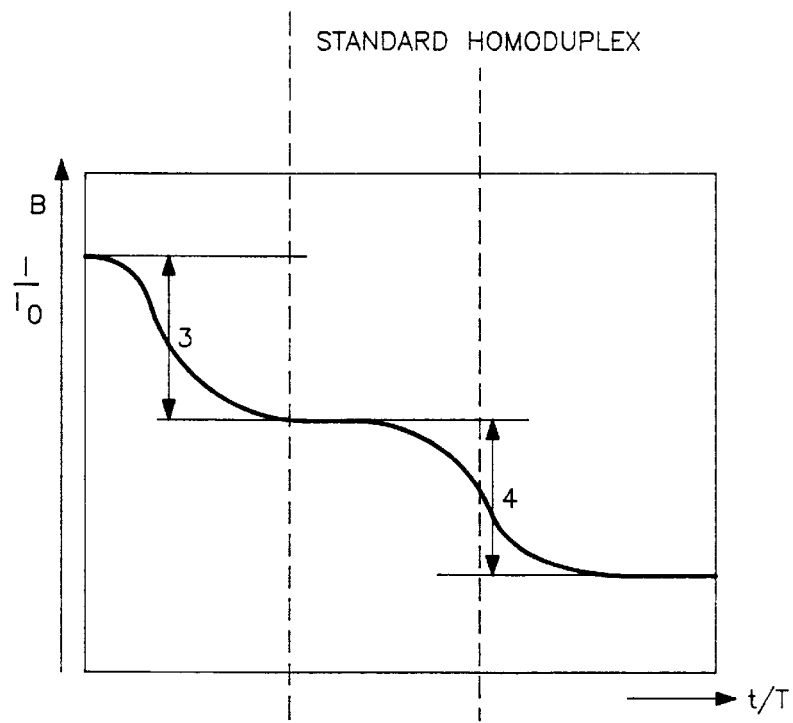
Figure 9C:
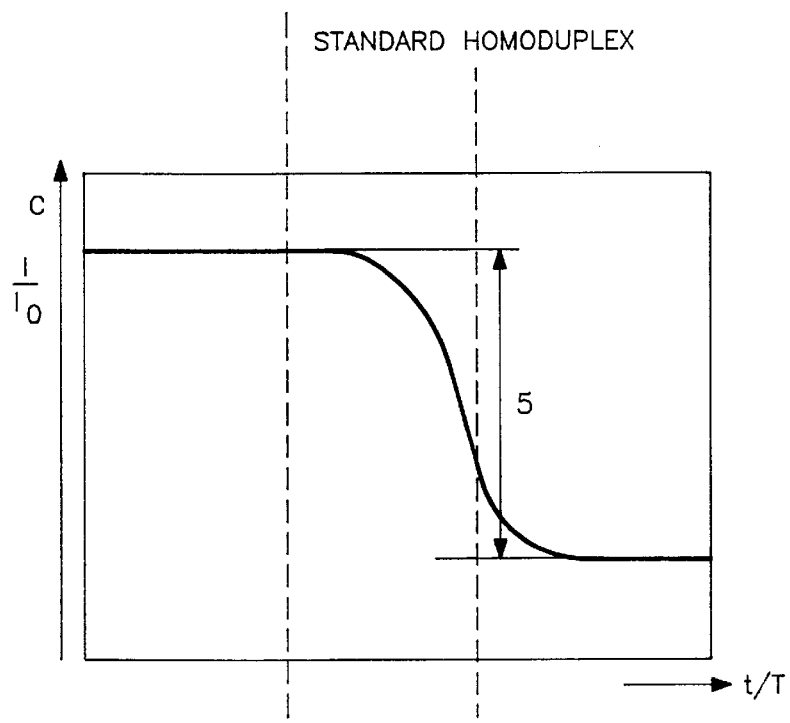
Figure 9D:
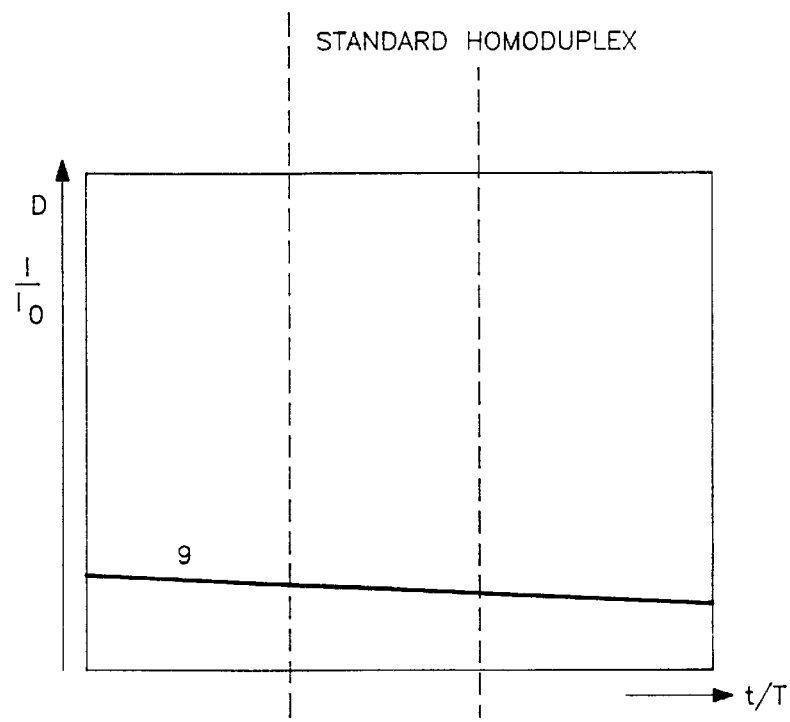
Figure 9E:
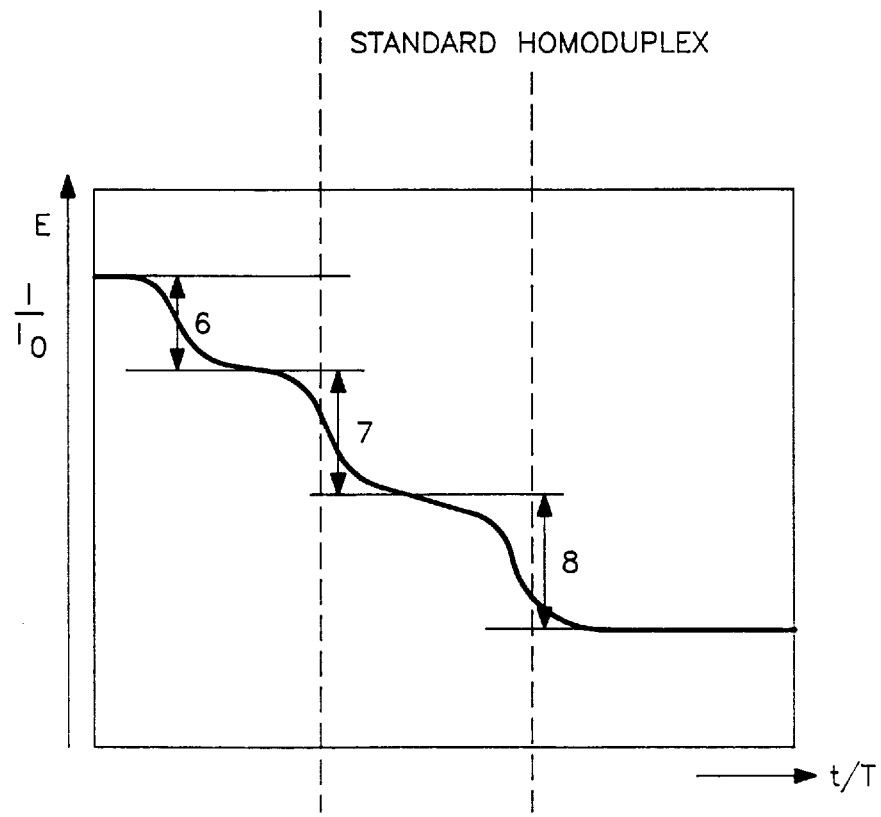

FIGS. 9a–9e schematically illustrate possible experimental results which may be obtained using the technique of the invention. At the ordinate, the fluorescence signal I is plotted in relation to the respective intensity ($I_0$) at the lowest experimental temperature (native). The x-axis describes the course of temperature in the heat-up process which preferably is linear over time. The two dotted lines mark the position of the standard homoduplex (A2) as well as the position of heteroduplex (A1) consisting of labeled probe and the wild type sequence (1) to be expected. In case the sequence to be analyzed bears at least one further mutation, stepwise decline of the fluorescence signal occurs already at lower temperature which is characteristic for the mutation (B3). The relative height of the steps to each other (1/2, 3/4, 6/7/8) directly represents the relative concentration ratio of the involved molecules. A result as in FIG. 9c is obtained when only the standard nucleic acid is amplified and the biological sample does not contain any corresponding nucleic acid or merely small amounts of same. A result as in FIG. 9d is obtained when the amplification reaction has proceeded improperly and not even the standard has been amplified. In case the biological sample contains more than one homologous nucleic acid species, this will give rise to several steps of the temperature-dependent course of fluorescence (6 and 7) which are different from each other (FIG. 9e).

Figure 10A:
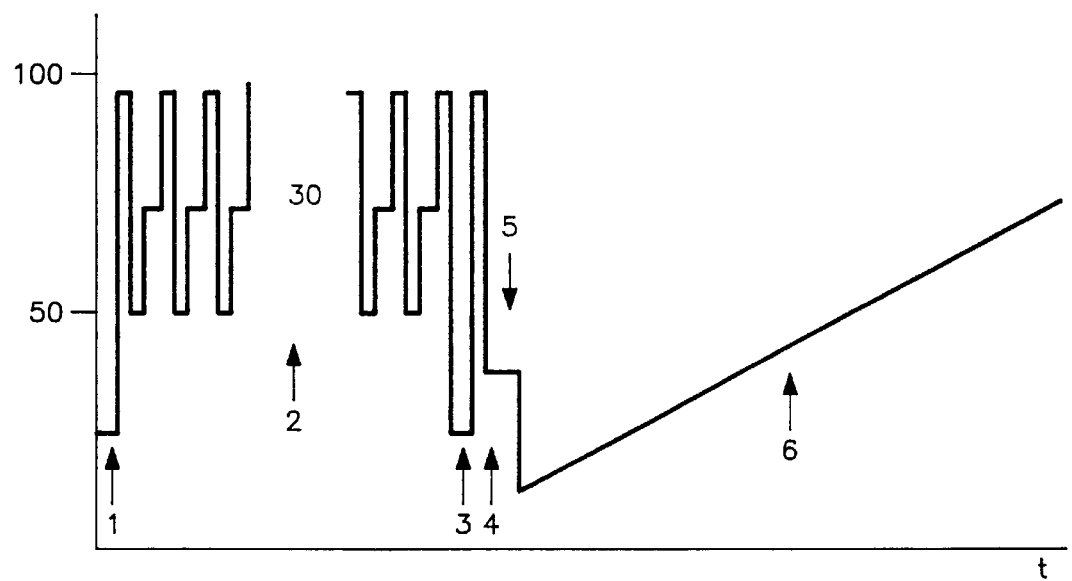
Figure 10B:
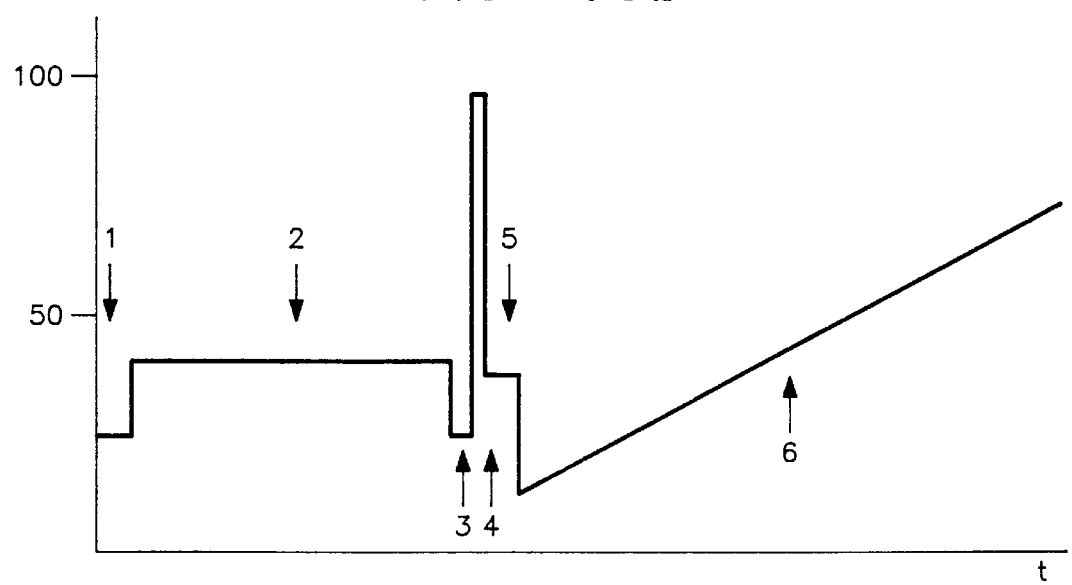

FIGS. 10a and 10b

FIGS. 10a and 10b describe the schematic course of temperature and the related single steps in the process according to the invention. In FIG. 10a, the course of analysis using the PCR technique is illustrated, in FIG. 10b, the course of an amplification at homogenous Temperature (37° C.), e.g., in the 3SR technique (see below), is given.

1) Addition of biological sample to the lyophilized amplification batch and sealing the reaction compartment.

2) Amplification at homogenous temperature or with use of temperature programs (PCR).

3) Admixing the labeled probe(s) in the hybridization buffer.

4) Denaturation step at 98° C.

5) Probe re-association with the amplified DNA.

6) Time/temperature gradient with optical on-line control.

FIG. 11

Figure 11:
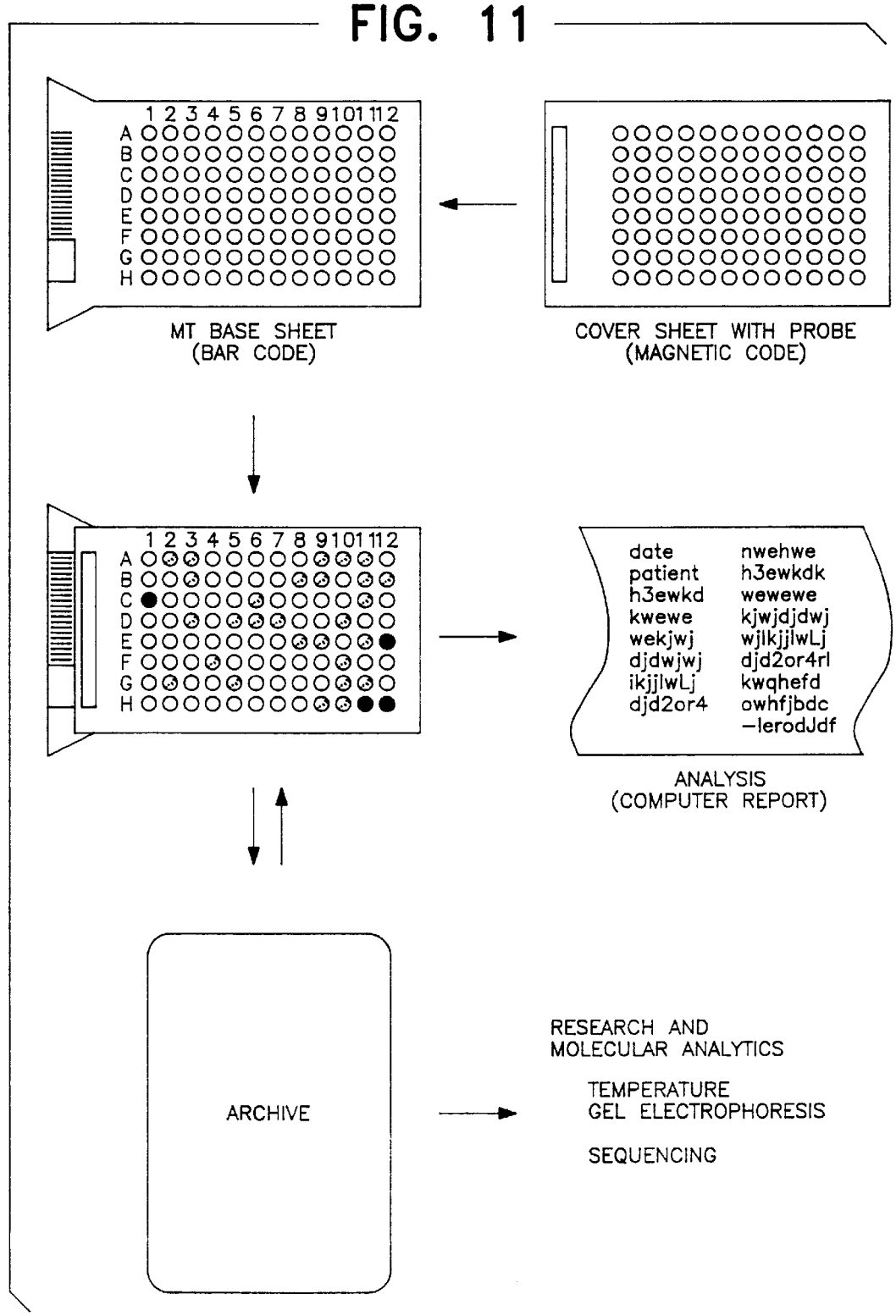

FIG. 11 schematically illustrates a possible embodiment of the process of the invention for automatized large-scale series. The assay kit includes the sheet components with the storable and ready-to-use reagents. The bar coding permits definition of assay type and allocation of positions. The write-on magnetic strip then is available for sample-specific data. Following analysis, the test sheets may be disposed off without opening or may be archived for possible further analyses.

FIG. 12

The schematic representation illustrates a special embodiment of the process according to the invention. A primer used for amplification is fixated to the surface of, e.g., magneto beads. For the purpose of amplification and hybridization, magneto beads can be maintained in the form of a suspension by a magnetic field; for the purpose of laser fluorescence observation, however, during the dissociation process induced by the temperature gradient they may be withdrawn from the solution and fixated at a defined spot. Thus, the laser beam may be directed directly to the particle surface, and the fluorescence during dissociation of the probe may be monitored specifically. This process succeeds, e.g., with use of a single melting domain and permits use of oligomeric, non-intercalating fluorescent dyes as optical markers.

Reaction and analysis may be carried out in a single reaction compartment. Preferably, a microtitration form is used which permits to simultaneously subject 96 samples or portions of 96 samples (strips of 8 or 16) to analytics. Preferably, the reaction vessel is constructed such that it has volumes of from 20 to 100 μl. Instead of single reaction vessels, sheets are preferably used which have hollows or recesses accommodating the samples. Per se known sheets (PCT/EP 89/01320, PCT/EP 89/01387, PCT/DE 91/0082, PCT/DE 91/00081, PCT/DE 91/00083) are specifically suitable for the process of the invention since they are thermostattable with particular efficiency, cheap in production and without problems in environmentally compatible disposal. The use of optically lucid sheets for the visible light region permits online registration of fluorescence signals of commercially available fluorescent dyes.

The sheets may be charged with generally required reagents (enzymes, primers, buffers, stabilizers, etc.) and preserved for long periods of time in lyophilized condition. Preferably, trehalose or saccharose are used as the stabilizers. Following addition of the samples to be analyzed, the reaction vessels arranged in series may be sealed hermetically. This may be effected by fusing a cover sheet with the sheet bearing the reaction compartments. Similarly, sheets can be used which are coated with a thermoplastic polymer and can be fused at below the melting temperature of the actual support sheets. In the cover region of the support sheet, above the reaction compartments, reagents may be fixated or placed in compartments, which are not to participate in the reaction process from the beginning. In the case of the invention this is, e.g., the specifically labeled probe which is lyophilized and stabilized in a buffer mixture required subsequent to amplification reaction for hybridizing the amplification product and the labeled probe. Subsequent to sealing the reaction compartments, the amplification reaction takes place at homogenous temperature (3 SR, Self-sustained Sequence Replication; TAS, Transcription based amplification system) [J. C. Guatelli et al., Proc. Natl. Acad. Sci. 87, 1874–1878 (1990); Kwoh, D. Y., Davis, G. R., Whitfield, K. M., Chapelle, H. L., Dimichele, L. J. & Gingeras, T. R. Proc. Natl. Acad. Sci. U.S.A. 86, 1173–1177, (1989)] or in a thermocycler as a polymerase chain reaction (PCR). In this step, standard and template are amplified at a constant ratio so that the reaction final product contains ca. from 100 ng to 1 μg of amplified nucleic acid.

Figure 1:
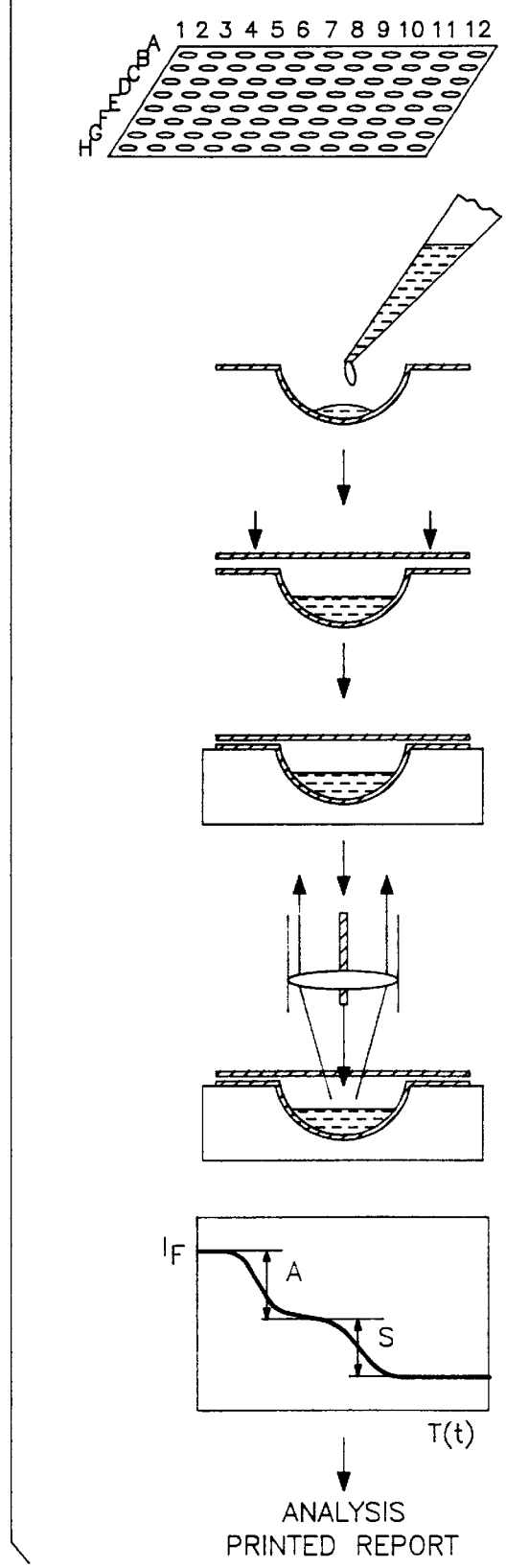
FIG. 1
Figure 2:
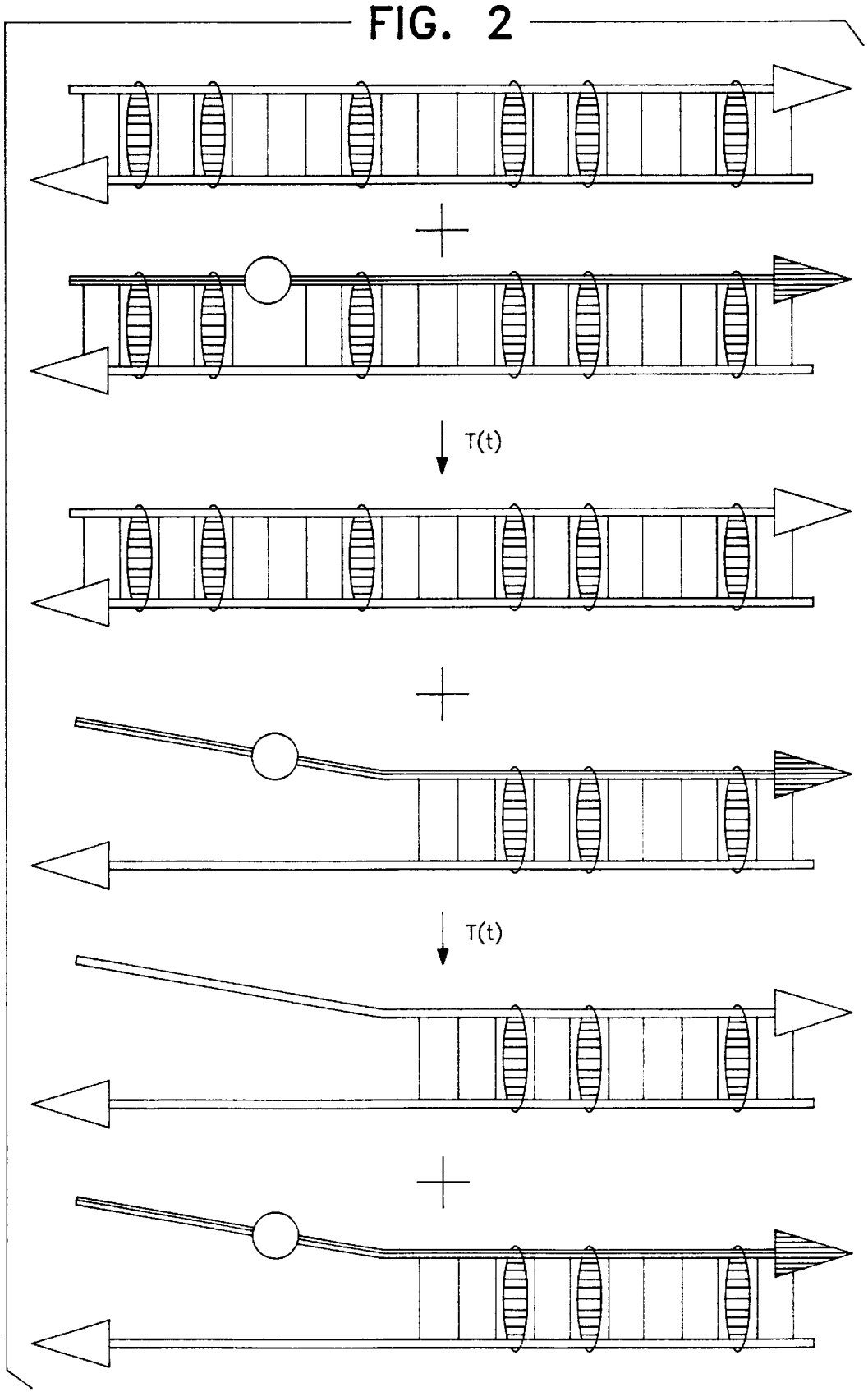

In a possible, technically very simple embodiment (FIG. 2), the reaction compartment includes a luminescent dye, preferably a fluorescent dye, preferably having intercalating properties, binding at multiple positions in double-helical structures and having modified spectroscopical properties in the bound state. When in the analysis to follow, using the time/temperature gradient, the corresponding double-stranded structures are denatured, the dye is liberated again. This process is recorded spectroscopically. However, a necessary condition for this procedure is to select the concentration of the free dye such that it is greater than the number of free binding sites. On the other hand, liberation of the dye from a double-strand region results in binding in another structure without change in fluorescence signal.

In another preferred embodiment, the aqueous solution of the reaction compartment is contacted with a fluorescent dye-labeled probe preferably stored in compartments at the sealing sheet to dissolve the probe (FIGS. 3 and 4). Following denaturation and renaturation, the probe is monitored by fluorescence spectroscopy. At low temperatures the probe is in the double-stranded hybrid with amplified standard (homoduplex) and amplified template (heteroduplex). Now, the reaction compartment is heated over time, preferably in linear fashion, where initially, the heteroduplex is denatured partially or completely and subsequently, the homoduplex is denatured partially or completely. From the relative ratios of the denaturation signals measured over the steps of decrease in fluorescence (FIGS. 9a to 9e), the template titer may be calculated precisely.

Preferably, a fluorescent marker is used as the denaturation signal. Particularly suitable for this purpose are fluorescent dyes possessing the property of strongly fluorescing only when incorporated between base pairs (intercalation). If such dyes are released from a double helix due to a denaturation process, this can be registered by a change in fluorescence intensity (decrease in fluorescence). Where double helices have different stabilities as is the case with homoduplex and heteroduplex, the signal changes will occur at different temperatures and may be analyzed and evaluated separately. Furthermore, the precise denaturation temperature reflects possible differences in sequence as an indicator for so-called virus drifts which may occur due to mutations.

Occasionally, intercalating dyes have another favorable property relating to the excited state half-life. In the case of ethidium bromide, the half-life of the excited state is greater by more than 10 fold if the fluorescent molecule is in the intercalated state. Thereby, a pulsed laser excitation may be used where in the subsequent phase of fluorescence emission, the fluorescence intensity can be measured without the influence of scattered light from light used for excitation. Using the process according to the invention, it is possible to employ dyes such as ethidium bromide, preferably at low concentrations (preferably from $10^{-10}$ to $10^{-7}$M).

Apart from direct fluorescence intensity measurement, a so-called Förster Transfer (energy transfer) between closely adjacent fluorophores or the parameter of fluorescence polarization may also be used according to the invention.

High specificity of the process according to the invention is achieved when using a probe covalently linked to one or more dye molecules (FIG. 4). Preferably, this is achieved by using a primer in the preparation of the probe, which terminally or internally bears at least one dye molecule. Only if the probe is in the state of base pairing of homoduplex or heteroduplex, maximum fluorescence intensity of the fluorescent dye intercalated in the double-strand is obtained. The fluorescence intensity of the reaction batches conducted in parallel may be observed simultaneously by using a camera. Single evaluation of the channels results in a fluorescence development as is representatively illustrated in FIG. 9. The relative heights of the fluorescence variations may be converted directly to copy numbers by a computer connected on-line.

In a further preferred embodiment of the process according to the invention, the reaction is carried out within the compartment, with partial coupling to a solid phase support (FIG. 12). The advantage of this procedure is founded thereon that by using laser optics it is possible to selectively measure the surface of a solid phase support or alternatively, the solution without the solid phase support. For practical operation, this means that a fluorescent dye may be used which does not necessarily change its measurable parameters via intercalation. Thus, probes having optional, oligomeric dyes may be used which permit to obtain an increase in fluorescence intensity by more than tenfold. The thermally induced denaturation process (see above) may then be monitored by measuring the dissociation of the probe from surface-bound, amplified nucleic acids (sample and standard) into the free solution, utilizing the decrease in fluorescence (dilution effect). This approach is confined to analyses where the double-strand region used for standardization lies within the thermodynamically most stable melting region of the nucleic acid, or where the probe has only one melting region.

Addition of a labeled probe subsequent to amplification may be abandoned if the probe is not capable of participating in the amplification process due to specific properties and performance of the amplification process. According to the invention, this may be accomplished if the probe is present in a thermodynamically stable double-stranded structure remaining stable during the amplification process and not participating in the reaction process. For example, labeled RNA double helices of high thermodynamic stability or chemically modified probes may be employed. In this fashion, the amplification process may be controlled such that the probe steadily remains double-stranded in the amplification reaction and does not participate in the amplification process, be it the case that the denaturation temperature is insufficient or enzymes involved will not amplify the double-stranded RNA or the modified probe.

Amplification techniques bear the great danger that subsequent to amplification, amplified DNA or RNA molecules might escape into the environment. Particular danger is constantly present due to aerosol formation which is difficult to control industrially. However, the process of the invention in its specific embodiment permits to carry out amplification reactions and analytics in a hermetically sealed reaction vessel and subsequently to dispose same in sealed condition. This provides a definite contribution to molecular laboratory hygiene and to reliability of results in routine diagnostics.

Routine diagnostics are closely associated with the necessity of archiving results and—if possible—the samples analyzed. Again, the process of the invention offers an almost ideal opportunity:

The sheets may be provided with a test-specific bar labeling and thus, may be characterized and compiled for data with respect to target assay, manufacturing date, expiry date, etc.

The sheets may be stored in a hermetically sealed and archived condition for prolonged periods of time.

Analyses may be repeated and checked at a later time.

In case the analytical method furnishes evidence for the presence of new interesting DNA/RNA variants, the sample mixture may be removed and preparatively separated on the flat temperature gel electrophoresis separation system and, e.g., may be subjected to sequence analysis.

For smaller series, temperature gradient gel electrophoresis had shown its reliability for quantitative amplification analytics. In this technique such PCR amplification products are preferably used which bear G:C-rich, primer-encoded sequences at the more stable fragment end. These so-called G:C clamps ensure the reversible course of melting required for temperature gel electrophoresis, and suppress untimely dissociation of the fragments into single strands. For a variety of analyses using temperature-dependent gel electrophoresis, G:C clamps which are expensive in use and may cause difficulties in amplification will no longer be required. Sequential liberation of fluorescent dyes in an assay may quite well be irreversible without distorting the result.

The process according to the invention has considerable economic significance for more economic manufacturing of the test kits as well as with respect to costs for operating the analytics. The operation may be automatized almost completely, and the result of the analysis may be printed in the form of a hard copy report. Thus, the temperature gel electrophoresis technique is not limited to expensive, quantifying analyses of great valuation but may also be employed for low-cost analyses. For example, this relates to the field of microbiology, human genetics, phytoanalytics, forensic analytics, and industrial research such as, e.g., research on active agents, i.e., screening of target substances for active agents which may be evaluated through DNA or RNA amplification or modification, down to simple toxicity assays.

The process according to the invention having its useful characteristics such as PCR/3SR/TAS amplification efficiency suitability for serial or single examinations on-line registration simultaneous nucleic acid qualification/quantification single-batch multi-component analysis elimination of danger of contamination by amplification products low costs of assay reagents and assay operation generally valid—no assay-specific—procedure guidelines permits new utilization prospects for amplification techniques such as PCR, 3SR or TAS.

In genetic analytics, efforts envisaging a long-term prospect are made which permit, for instance, to detect severe genetic diseases from traces of biopsy material or amniotic fluid. Here, the burden of costs for such large-scale programs likewise is a decisive limitation as is the fact that only in very few cases analysis of a single gene locus is sufficient to permit statements regarding the transmission potential. For the most frequent lethal hereditary disease among the Caucasian population, the cystic fibrosis, more than 18 further mutations in addition to the initially discovered mutation (Delta 508) have been described, which may induce mucoviscidosis. The process of the invention permits parallel analysis of a great number of loci, with minor additional expense, and if necessary—without great additional expense—to cover further assay items. For example, the process of the invention also permits to examine point mutations responsible for certain genetic diseases. Hitherto, such diseases can only be diagnosed using the allele-specific oligonucleotide hybridization technique (ASO) which is very difficult to handle.

Of similar significance is the technique for thalassemia screenings.

Thus, it becomes clear that the process according to the invention can simplify the previous methods for detecting defined mutations and design them to be substantially lower in costs. Instead of an artificially introduced mutation, in order to make norms or standards, the desired, naturally occurring mutant may be employed or used as a probe. Thus, for operating the process according to the invention, all those assays are possible which are carried out using, e.g., differential oligonucleotide hybridizations as filter assays.

Epidemiological studies on infectious and hereditary diseases emerge as an increasingly important working field for international medicine. One may remind the alarming rate of propagation of modern viral diseases such as AIDS (HIV) caused by the changed sociobiological structures. One decisive precondition for vaccination and therapy approaches is an epidemiological registration of the actual situation as comprehensive and careful as possible with epidemiological-prognostic significance. This relates not only to the actual appearance of the virus but also to the geographic distribution of its spectrum of variants, with data-level registration of the symptoms and signs of the disease. Only by profound automatized analytics such studies will become economically justifiable.

For quite a time, pharmaceutical research touches the limits of what it feasible in its very own fields of activity. Many attempts have been made to combat the obvious limitations of conventional pharmaceutical research by virtue of new conceptions. Reference is made to the example of strategic-intelligent drug design which is to permit well-aimed synthesis of effector molecules having precalculated structure on the basis of well-founded knowledge about a target structure such as that of a receptor and thus, to replace conventional screening methods. A second strategy with a promising future is evolutionary biology with its potential, utilizing evolutionary systems, to generate substances having the desired activity potential. Future pharmaceutical research has to avoid personnel-intensive, randomized synthesis programs for both cost- and project-related reasons.

Here, the process according to the invention may provide an important contribution. The suitability for screenings using quantifying DNA/RNA assays at low cost permits to develop new assays for automatized detection of active substances in oncology, with viral and bacterial infections and assays for toxicological studies. One could think of new assay systems in combination with cellular in vitro systems which will increasingly replace animal models. Neither must one forget that time periods for cultivation and assays will be cut down substantially since, e.g., variations on the mRNA level are detected immediately without the necessity to time-consumingly measure cellular subsequent reactions. For a number of assays it might become possible to replace transformed cell cultures by primary cultures, e.g., from blood. Simultaneous high sensitivity would also allow for registering differentiation parameters to measure cell type-specific activities. For example, one could think of certain leucocyte subpopulations (macrophages, T4 cells, etc.) with their characteristic receptor functions and infectability by viruses such as HIV.

Biological experiments with recombinant systems, particularly open-air experiments require from both science and environmental protection careful analytics of genes, registration of gene persistence in populations, gene variations, and gene activities. As an example, there may be mentioned antiviral therapies on plants where the attempt is made to create virus resistance against certain viruses by designing transgenic plants which produce viral envelope proteins and thus, protect the plant from infection by an exogenic virus. open-air experiments or interbreedings into naturally occurring populations require precise knowledge, for example:

How is the segregation behavior of the recombinant plants with respect to the recombinant locus?

How active are envelope protein genes in relation to population and number of generations?

How does the viral target organism react to the new selection stress?

Here, the process according to the invention permits screenings and, in particular, registration of sample collectives in one single assay to obtain quantitative statements about populations. At the same time, it becomes possible to monitor drift phenomenons in development of resistance.

Traditionally, microbiological assays in bacteriology have been conducted by cultivation or direct dot hybridization. Hitherto, such assays could not be displaced by more profound assays just for the aspect of costs alone. The process according to the invention can completely change this situation. In this process, it is not a decisive issue of costs if a sample has to be assayed for multiple pathogens simultaneously, or if a pathogen has to be analyzed in an antibiogram.

The last-mentioned type of analysis may play a major role particularly in virological analyses if virus resistances have to be tested or registered quantitatively. To virology, the process of the invention is advantageous since it permits greatly simplified analytics by combining culturing and testing process of a virus propagation, which is favorable in cost and lower in expense.

The food industry primarily has conducted extensive controls to examine some specific microbiological classes of pathogens, setting out, however, from a variety of sample substances of starting materials, of process steps, of equipment containments, and of final products. In similar fashion as in the pharmaceutical industry, processing involves large-scale batches of considerable economic value. Here, minimizing the durations of analyses, combined with reliable test results are critical factors. For example, salmonellal assays frequently require time-consuming pathogen culturing processes. The process according to the invention, with its likewise quantitative results in screenings makes it possible to abandon culturing processes and saves costly process operation steps and storage.

Frequently, phytopathological analyses are prohibitively costly. Even if, as a rule, only representative sample collectives of seed or ornamental and useful plants are delivered to analysis, for example, for virus infection, the number of samples so far permitted almost exclusively immunological ELISA processes for cost reasons, which often do not work at all or unsatisfactorily. Hence, phytoanalytics require modified concepts of analyzing to meet the demands. These concepts are provided by the process of the invention.

As now, for the first time, RNA parameters have been found which permit precise analysis of forest damage (Riesner et al., in preparation), the process according to the invention allows for the set-up of an extensive program for registration of forest damages as well as their temporal and geographic spreading.

Research in molecular biology increasingly strives for analytic processes suitable for application in series in order to, for example, successfully carry out the so-called HUGO project on complete elucidation of the human genome sequence and of genomes of other important organisms. In future, this project will not only have the object of completely analyzing a single genome but also to analyze certain loci having disease-related potential, as is necessary—for comparison—in identity examinations (HLA analytics, haplotype association, genetic variability, etc.).

The process according to the invention makes it possible on a DNA level (amplified loci, gene dosage) and on a mRNA level to monitor expression optimizing, promoter controlling, etc., and to utilize same in the screening or mutagenesis process. Here, the process has proven to be an important complementary technique to "cell sorting".

We claim:

1. A process for the qualitative and quantitative analysis, in a reaction means comprising a sealed reaction chamber, of at least one in vitro amplified nucleic acid in a sample comprising the steps of:

including in the sample, during or subsequent to amplification of the nucleic acid, at least one probe being an oligo- or polynucleotide that hybridizes with the nucleic acid, and dye that intercalates with the nucleic acid, or a combination thereof, and which interacts with the nucleic acid to be detected, said probe having a spectroscopically measurable parameter;

exposing the sample to the action of a gradient that, at least partially, denatures the amplified nucleic acid in the sample and that effects variation in the spectroscopically measurable parameter of the probe, creating a measurable signal;

detecting the measurable signal; and optionally carrying out the amplification reaction and the qualitative and quantitative analysis without opening the sealed reaction chamber.

2. The process according to claim 1, wherein the spectroscopically measurable parameter of the probe is at least one luminescent or fluorescent dye, and the probe includes a nucleic acid portion, which interacts with the in vitro amplified nucleic acid during the denaturation accompanied by a change in the measurable signal.

3. The process according to claim 1, wherein the measurable signal is detected (a) using wave length variation, shift in luminescence or fluorescence intensity, variation in fluorescence polarization, variation in excited state lifetime, or a combination thereof, or (b) using the principle of energy transfer, or (c) through a concentration effect.

4. The process according to claim 1, wherein the spectroscopically measurable parameter includes a plurality of dyes distinguishable from each other spectroscopically.

5. The process according to claim 4, wherein a laser excites luminescence of the dyes.

6. The process according to claim 1, wherein the reaction mixture includes at least one co-amplified nucleic acid standard, the sequence of which is homologous to a sequence to be analyzed, with the exception of at least one point mutation.

7. The process according to claim 1, that includes at least one co-amplified nucleic acid standard having a primer region, the sequence of which is homologous to the primer region of the amplified nucleic acid.

8. The process according to claim 7, wherein the nucleic acid standard is a natural component of the amplified nucleic acid.

9. The process according to claim 1, wherein amplification is carried out (a) in free solution or (b) using a primer attached to a solid phase, the amplified nucleic acid hybridizes with the probe, and the analysis is determined either attached to the solid phase or within the free solution.

10. The process according to claim 7, wherein the probe is is at least one molecule of fluorescent dye linked to a nucleic acid molecule, the sequence of which is identical or homologous to the amplified nucleic acid to be detected or to the co-amplified nucleic acid standard.

11. The process according to claim 10, wherein the fluorescent dye linked to the nucleic acid molecule is added to the reaction mixture after completing amplification, and is hybridized with the amplified nucleic acid by thermal denaturation with subsequent renaturation.

12. The process according to claim 10, wherein the fluorescent dye linked to the nucleic acid molecule is added to the reaction mixture prior to completing amplification, and the probe is a non-amplifiable double-stranded RNA or a non-amplifiable chemically modified nucleic acid.

13. The process according to claim 1, wherein a primer of a primer pair is used for the amplification, which primer encodes a G:C-rich region at the 5' terminus.

14. The process according to claim 1, wherein the probe is an oligo- or polynucleotide having at least two chemical structural elements, wherein (a) each chemical structural element can be detected, upon interacting with electromagnetic waves, by absorption or emission of radiation and (b) one of the structural elements, upon interacting with electromagnetic waves, can link to another position on the oligo- or polynucleotide.

15. The process according to claim 14, wherein the chemical structural elements have a chromophoric system.

16. The process according to claim 15, wherein the chromophoric system luminesces via a dye substituent thereon.

17. The process according to claim 14, wherein the chemical structural element that can link to another position on the oligo- or polynucleotide is a photochemical crosslinker.

18. The process according to claim 17, wherein the photochemical crosslinkers are psoralene or a psoralene derivative.

19. The process according to claim 14, wherein spacing between the two chemical structural elements is between 8 to 12 nucleotide positions.

20. The process according to claim 1, wherein the reaction means comprises a plurality of recesses in a sheet system, each recess thermally weldable, accommodates ready-for-use reagent mixtures in lyophilized or matrix-bound form, and permits direct optical measurement.

21. The process according to claim 20, wherein the reagent mixtures are stored in spatially separated matrices, and, subsequent to sealing the reaction chamber, are introduced into the reaction process.

22. The process according to claim 1, wherein the analysis is effected by microtitration.

23. The process according to claim 1, wherein the gradient is a time-controlled temperature gradient, and the variation of the spectroscopically measurable parameter is monitored as a function of time, temperature, or time and temperature.

24. The process according to claim 23, wherein the analysis is by temperature gel electrophoresis, chromatography, or directly in homogenous solution, or a combination thereof.

25. The process according to claim 24, wherein the presence, number, homology, or combination thereof of the amplified nucleic acid depends on the monitored spectroscopically measurable parameter.

26. The process according to claim 1, wherein the analysis is effected using a data processing system.

27. The process of claim 1 wherein the probe is an oligo- or polynucleotide having at least one chemical structural element (a) having a stable bond that, upon interacting with electromagnetic waves, is capable of cleavage and subsequent linkage with the amplified nucleic acid and (b) that can be detected, upon interacting with electromagnetic waves, by absorption or emission of radiation, wherein said structural element is not a purine or pyrimidine substituent of naturally occurring nucleotide components.

28. The process of claim 27 wherein the chemical structural element having a stable bond is psoralene or a psoralene derivative.

29. The process of claim 27 wherein the chemical structural element that can be detected luminesces.

30. The process of claim 27 wherein one of the chemical structural elements is located 8 to 12 nucleotides away from another of the chemical structural elements.

31. The process of claim 1 wherein the reaction means includes (A) at least one multiple-well-containing sheet, each well being a reaction chamber that includes the probe for and lyophilized amplification reagents and (B) a sealing sheet cooperating with the multiple-well-containing sheet in a manner independently sealing each reaction chamber with a seal that becomes an interior surface of the reaction chamber.

32. The process of claim 31 wherein the reagents are present in at least one water-soluble matrix.

33. The process of claim 32 wherein the matrix includes a stabilizer.

34. The process of claim 32 wherein the matrix includes a sugar.

35. The process of claim 32 wherein the matrix includes trehalose or saccharose.

36. The process of claim 32 wherein the reagents include amplification primers, buffer components, at least one polymerase, and co-factors.

37. The process of claim 31 wherein the reagents include amplification primers, buffer components, at least one polymerase, and co-factors.

38. The process of claim 31 wherein at least one reaction chamber of the well-containing sheet includes a reagent/probe-containing matrix and the chamber interior surface of the corresponding seal includes hybridization reagents.

39. The process of claim 31 wherein the reaction means is composed of kit systems.

40. The process of claim 1 including computer-controlled, time-dependent thermostating of the reaction chamber.

41. The process of claim 1 including optical-excitation-effecting emitting of a fluorescence signal and optical detection of the fluorescence signal.

42. The process of claim 41 wherein the excitation is by a laser.

43. The process according to claim 13, wherein said primer has from 15 to 20 G:C residues at the 5' terminus.

* * * * *

UNITED STATES PATENT AND TRADEMARK OFFICE
CERTIFICATE OF CORRECTION

PATENT NO.   : 5,871,908
DATED        : February 16, 1999
INVENTOR(S)  : Henco et al.

It is certified that error appears in the above-identified patent and that said Letters Patent is hereby corrected as shown below:

Column 16,
Lines 61 through 66, should read:

-- including in the sample, during or subsequent to amplification of the nucleic acid, at least one probe which interacts with the nucleic acid to be detected, said probe being an oligo– or polynucleotide that hybridizes with the nucleic acid, a dye that intercalates with the nucleic acid, or a combination thereof, and having a --

Column 17,
Line 45, delete "is" second occurrence.

Signed and Sealed this

Fifth Day of November, 2002

*Attest:*

JAMES E. ROGAN
*Attesting Officer*        Director of the United States Patent and Trademark Office

(12) EX PARTE REEXAMINATION CERTIFICATE (9953rd)
United States Patent
Henco et al.

(10) Number: US 5,871,908 C1
(45) Certificate Issued: Nov. 21, 2013

(54) PROCESS FOR THE DETERMINATION OF IN VITRO AMPLIFIED NUCLEIC ACIDS

(75) Inventors: Karsten Henco, Erkeath (DE); Manfred Elgen, Göttingen (DE); Detley Riesner, Dusseldorf (DE)

(73) Assignee: Evotec AG, Hamburg (DE)

Reexamination Request:
No. 90/012,368, Jun. 21, 2012

Reexamination Certificate for:
Patent No.: 5,871,908
Issued: Feb. 16, 1999
Appl. No.: 08/157,195
Filed: Dec. 8, 1993

Certificate of Correction issued Nov. 5, 2002

(21) Appl. No.: 90/012,368

(22) PCT Filed: Feb. 4, 1993

(86) PCT No.: PCT/EP93/00254
§ 371 (c)(1),
(2), (4) Date: Dec. 8, 1993

(87) PCT Pub. No.: WO93/16194
PCT Pub. Date: Aug. 19, 1993

(30) Foreign Application Priority Data

Oct. 9, 1992 (DE) .................................... 42 34 086
Feb. 4, 1993 (DE) .................................... 42 03 178

(51) Int. Cl.
*B01L 7/00* (2006.01)
*C12Q 1/68* (2006.01)

(52) U.S. Cl.
CPC ............... *B01L 7/52* (2013.01); *C12Q 1/6825* (2013.01); *C12Q 1/686* (2013.01)
USPC ........................................ 435/6.11; 435/91.2

(58) Field of Classification Search
None
See application file for complete search history.

(56) References Cited

To view the complete listing of prior art documents cited during the proceeding for Reexamination Control Number 90/012,368, please refer to the USPTO's public Patent Application Information Retrieval (PAIR) system under the Display References tab.

*Primary Examiner* — Sharon Turner

(57) ABSTRACT

A process for the qualitative and quantitative determination of at least one in vitro amplified nucleic acid in a sealed reaction chamber,
wherein during or subsequent to the amplification of the nucleic acid at least one substance (probe) is present which interacts with the nucleic acid to be detected;
wherein spectroscopically measurable parameters of said substance (probe) are subject to variation, creating a measurable signal;
wherein the sample to be measured is exposed to the action of a gradient capable of at least partially denaturing nucleic acids;
with detection of the measurable parameter undergoing variation through the action of the gradient; and
the entire amplification reaction, including qualitative and quantitative determination, may be carried out in a sealed reaction chamber (measuring compartment) without intermittent opening,
permitting to automatically operate the diagnostic method of DNA and RNA amplification in qualitative and quantitative fashion on large series of samples.

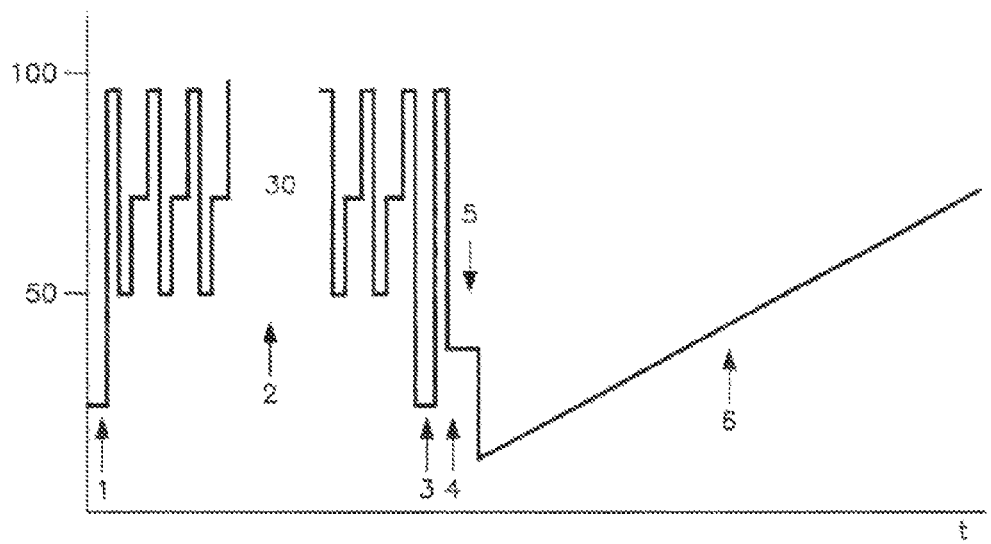

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 24 are determined to be patentable as amended.

Claims 6-9, 13, 23, 25-26, 40, 41 and 43, dependent on an amended claim, are determined to be patentable.

Claims 2-5, 10-12, 14-22, 27-39 and 42 were not reexamined.

1. A process for the qualitative and quantitative analysis, in a reaction means comprising a sealed reaction chamber, of at least one in vitro amplified nucleic acid in a sample comprising the steps of:

including in the sample, during or subsequent to amplification of the nucleic acid, at least one probe which interacts with the nucleic acid to be detected, said probe being an oligo- or polynucleotide that hybridizes with the nucleic acid, a dye that intercalates with the nucleic acid, or a combination thereof, and having a spectroscopically measurable parameter;

exposing the sample *subsequent to amplification* to the action of a *linear temperature* gradient that, at least partially, denatures the amplified nucleic acid in the sample and that effects variation in the spectroscopically measurable parameter of the probe, creating a measurable signal;

detecting the measurable signal; and

[optionally] carrying out the amplification reaction and the qualitative and quantitative analysis without opening the sealed reaction chamber.

24. The process according to claim 23, wherein the analysis is [by temperature gel electrophoresis, chromatography, or] directly in homogenous solution[, or a combination thereof].

* * * * *